US00PP37007P2

(12) United States Plant Patent
Nielsen et al.

(10) Patent No.: US PP37,007 P2
(45) Date of Patent: Oct. 7, 2025

(54) ***PENNISETUM* PLANT NAMED 'TUS022'**

(50) Latin Name: *Pennisetum advena*
Varietal Denomination: TUS022

(71) Applicant: Grzegorz Tuszynski, Otrebusy (PL)

(72) Inventors: Kim Nielsen, Ringe (DK); Tine Fogh Nielsen, Ringe (DK)

( * ) Notice: Subject to any disclaimer, the term of this patent is extended or adjusted under 35 U.S.C. 154(b) by 0 days.

(21) Appl. No.: 19/066,727

(22) Filed: Feb. 28, 2025

(51) Int. Cl.
*A01H 5/02* (2018.01)
*A01H 6/46* (2018.01)

(52) U.S. Cl.
USPC ..... Plt./384
CPC ..... *A01H 6/4654* (2018.05)

(58) Field of Classification Search
USPC ..... Plt./384
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Pennisetum* plant named 'TUS022' is disclosed, characterized by dark bronze red foliage color, and pink flower plumes changing to creamy-white. Plants are compact, low-maintenance and drought resistant. The new variety is a *Pennisetum*, typically produced as an outdoor ornamental plant.

2 Drawing Sheets

Latin name of the genus and species: *Pennisetum advena.*
Variety denomination: 'TUS022'

BACKGROUND OF THE INVENTION

The new cultivar was discovered by the inventor as a naturally-occurring mutation of an unnamed, unpatented specimen of *Pennisetum advena rubrum*. The new variety was found in September of 2022 as a single whole plant mutation in a container at a nursery in Ringe, Denmark.

Asexual reproduction of the new cultivar 'TUS022' was first performed in Ringe, Denmark by vegetative division in 2022. Subsequently, at least 6 generations of 'TUS022' have been reproduced and have shown that the unique features of this cultivar are stable and reproduced true to type.

SUMMARY OF THE INVENTION

The cultivar 'TUS022' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TUS022'. These characteristics in combination distinguish 'TUS022' as a new and distinct *Pennisetum* cultivar:

1. Compact size.
2. Dark bronze red foliage.
3. Pink flower plumes changing to creamy-white.
4. Low maintenance and drought resistant.

PARENT COMPARISON

Plants of the new cultivar 'TUS022' are similar to plants of the parent in most horticultural characteristics, however, 'TUS022' differs in the following:

1. Plants of the new variety are a dwarf version of plants of the parent.

COMMERCIAL COMPARISONS

Plants of the new cultivar 'TUS022' can be compared to the commercial variety *Pennisetum* 'Summer Samba', unpatented. Plants of the new cultivar 'TUS022' are similar to plants of 'Summer Samba' in most horticultural characteristics, however, 'TUS022' differs in the following:

1. Plants of the new variety are much smaller than plants of this comparator.
2. Plants of the new variety produce more flowers than plants of this comparator.

Plants of the new cultivar 'TUS022' can be compared to the commercial variety *Pennisetum setaceum* 'Fireworks', U.S. Plant Pat. No. 18,504. Plants of the new cultivar 'TUS022' are similar to plants of 'Fireworks' in most horticultural characteristics, however, 'TUS022' differs in the following:

1. Foliage color of the new variety is a dark bronze red, while the foliage color of this comparator is a brighter red.
2. Plants of the new variety are not as compact as plants of this comparator.

BRIEF DESCRIPTION OF THE PHOTOGRAPHS

Figure 1:
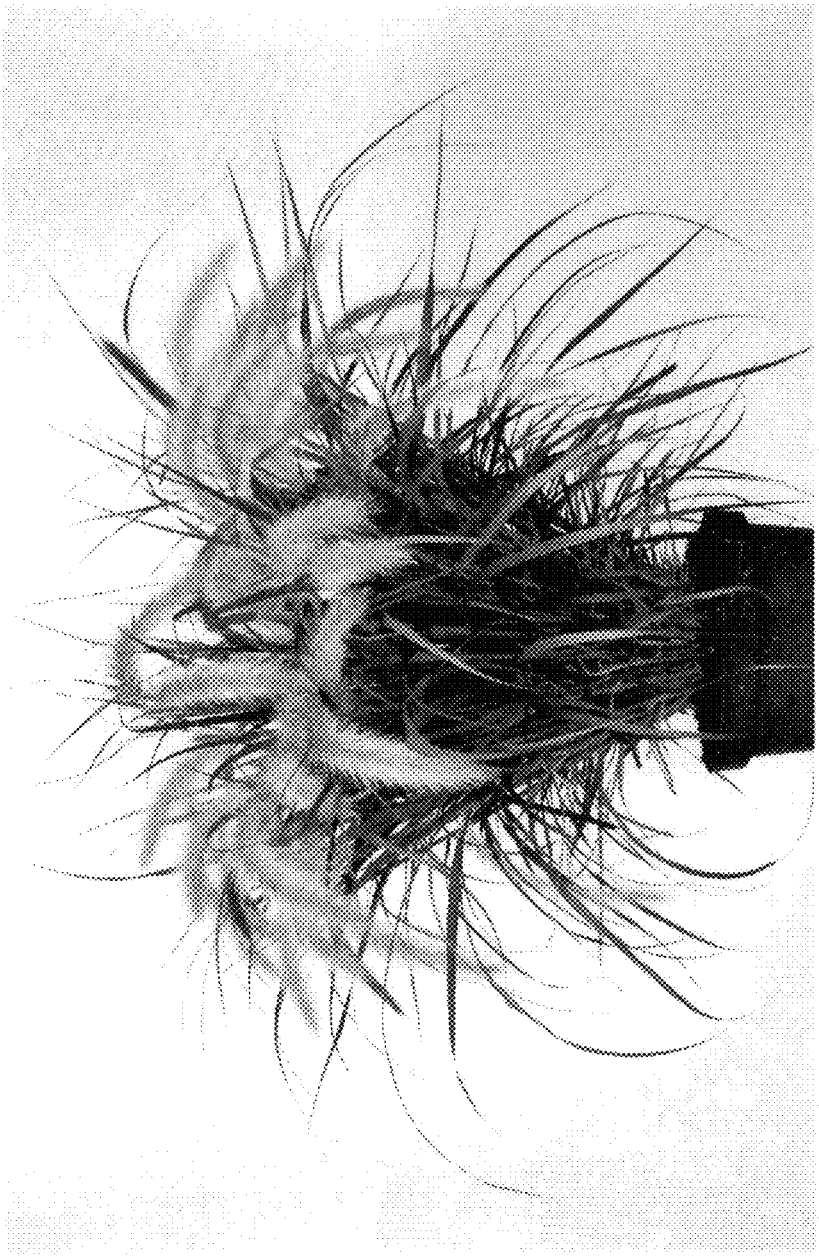

The accompanying photograph in FIG. 1 illustrates in full color a typical plant of 'TUS022' grown outdoors in Ringe, Denmark. This plant is approximately 2 years old, shown growing a 19 cm container.

Figure 2:
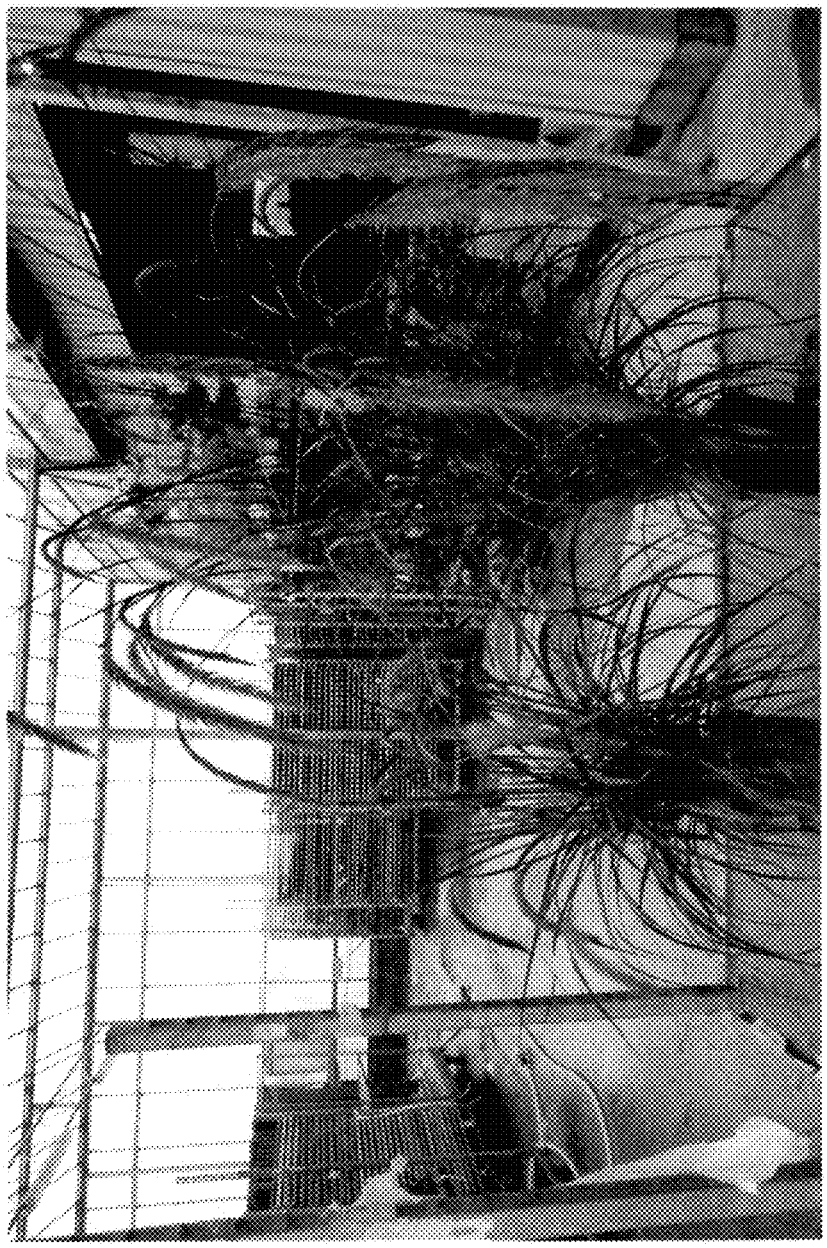

FIG. 2 is a comparison with the parent. 'TUS022' is on the left of the photo, the taller plant on the right is the parent.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart $6^{th}$ edition 2019, except where general terms of ordinary dictionary significance are used. The following observations and measurements describe 'TUS022' plants grown in 19 cm containers in Ringe, Denmark. Temperatures ranged from 10° C. to 20° C. at night to 18° C. to 30° C. during the day. No artificial light, photoperiodic treatments or chemical treatments were given to the plants. Measurements and numerical values represent averages of typical plant types. Plants were approximately 2 years old when described.

Botanical classification: *Pennisetum advena* 'TUS022'.

PLANT

Plant type: Herbaceous perennial grass.

Growth habit: Basal leafy shoots, with inflorescences carried in between the foliage.

Plant shape: Flattened globular.

Height: Average 53 cm to top of foliar plane; 46 cm to top of floral plane.

Plant spread: Average 72 cm.

Growth rate: Moderate.

Vigor: Moderate to high.

Branching characteristics: Leaves in basal leafy shoots, no main branches or lateral branches present.

FOLIAGE

Leaf:

*Arrangement*.—Alternate, growing in basal leafy shoots.

*Compound or single*.—Single.

*Quantity of leaves per shoot*.—Average 7.

*Length*.—Average 33.9 cm, excluding sheath.

*Width*.—Approximately 1 cm.

*Apex*.—Narrow acuminate.

*Base*.—Sheathing.

*Sheath length*.—Average 7.5 cm.

*Sheath width*.—Average 0.6 cm.

*Sheath color*.—RHS Yellow-Green 144A, strongly tinged Yellow-Green 148A to Greyed-Green 197A towards the ligule.

*Shape of blade*.—Linear.

*Aspect*.—Slightly carinate.

*Margin*.—Very finely toothed, feeling smooth when rubbed towards apex and feeling rough/sharp when rubbed towards ligule.

*Texture of top surface*.—Glabrous, smooth.

*Texture of bottom surface*.—Glabrous, smooth.

*Pubescence*.—None.

*Rugosity*.—Both sides non-rugose.

*Luster, upper side*.—Moderately glossy.

*Luster, under side*.—Moderately glossy.

*Color*.—Young foliage upper side: RHS Yellow-Green 146A, fading to Brown N200A towards the apex. Young foliage under side: RHS Yellow-Green 146A, fading to 147A and Brown N200A towards the apex. Mature foliage upper side: Blend of RHS Brown 200A and N200A, tinged Greyed-Purple 187A. Some streaking near Yellow-Green 147A. Mature foliage under side: RHS Yellow-Green 147A, flushed Brown N200A, and Greyed-Purple 187A.

*Venation*.—Type: Parallel. Color, upper side: RHS Brown 200A flushed Greyed-Purple 187A. Color, under side: RHS Yellow-Green 147A.

Petiole: Not present, leaves sheathing.

Other leaf characteristics: Ligules sparsely to moderately pubescent with thin hairs, average length of hairs: 0.2 cm, colored white; too small and too sparsely present to be measured with R.H.S.-CC.

INFLORESCENCE

Inflorescence:

*Type and form*.—Panicle.

*Height*.—Average 18.6 cm.

*Diameter*.—Average 4.5 cm.

*Quantity of flowers per inflorescence*.—Average 130.

*Quantity of flowers per plant*.—Average 5,000.

*Quantity of flower buds per plant*.—Average 5,000.

*Quantity of flowers and flower buds per plant*.—Average 10,000.

*Natural flowering season*.—Late summer.

*Time to flower or response time*.—Average 10 months.

Flower bud:

*Length*.—Average 0.5 cm, excluding bristles; average 1.7 cm including bristles.

*Diameter*.—Average 0.1 cm, excluding bristles; average 0.4 cm including bristles.

*Shape*.—Lanceolate.

*Texture*.—Smooth, glabrous, covered by bristly hairs extending from the base of the floret.

*Luster*.—Moderately glossy.

*Color*.—RHS Yellow-Green 148A and 148B, bristles Greyed-Purple 187B and 187C.

Flower:

*Type and form*.—Single, flowers consisting of 2 glumes, and 2 lemmas, covered by bristly hairs extending from the base of the floret.

*Aspect*.—Arching.

*Flowering habit*.—Very freely.

*Fragrance*.—None.

*Shape*.—Single.

*Height*.—Average 1.1 cm.

*Diameter*.—Average 1.1 cm.

*Length*.—Average 2.6 cm.

*Longevity on plant*.—Average one month.

*Persistence*.—Persistent.

Petals:

*Type or form*.—Flowers consisting of 2 glumes and 2 lemmas, covered by bristly hairs extending from the base. 2 glumes near oppositely placed at the base of each individual flower, 2 lemmas near oppositely placed above glumes.

*Texture*.—Glumes and lemmas glabrous, matte.

*Shape*.—Glumes and lemmas, strongly concave.

*Margin*.—Glumes and lemmas, entire.

*Base*.—Glumes and lemmas, cuneate.

*Apex*.—Glumes and lemmas, narrow acute.

*Length*.—Glumes: Lower: 0.2 cm. Upper: 0.6 cm. Lemma: Lower: 0.5 cm. Upper: 0.5 cm.

*Width*.—Glumes: Lower: About 0.1 cm. Upper: About 0.1 cm. Lemma: Lower: About 0.1 cm. Upper: About 0.1 cm.

*Color*.—When opening and at maturity, both sides: Lower Glume: RHS Yellow-Green 145C. Upper Glume: RHS Yellow-Green 145C, fading to 146D towards apex. Lower Lemma: RHS Yellow-Green 145C, fading to 146D towards apex. Upper Lemma: RHS Yellow-Green 145C, fading to 146D towards apex.

*Venation*.—No venation visible.

*Pubescence*.—One whorl of bristly hairs extending from the base of the floret, average length: 1.8 cm, colored RHS Greyed-Purple 187B and 187C. Hairs extending as flowers age, to an average length of 2.4 cm. Glumes and lemmas not fading; bristly hairs fading RHS Grey-Brown 199B to 199D.

Calyx/sepals: No separate calyx and corolla visible.

Peduncles:

*Terminal length*.—Average 30.7 cm.

*Terminal diameter*.—Average 0.2 cm.

*Angle to lateral branch axis*.—Average 0° (=straight on top of stem).

*Strength*.—Moderately strong.

*Texture*.—Smooth, glabrous.

*Luster*.—Matte.

*Color*.—RHS Green 137C and 137D.

Pedicels:

*Length*.—Average 0.1 mm.

*Diameter*.—Average 0.5 mm.

*Angle to peduncle axis*.—Average 40°.

*Strength*.—Moderately strong.

*Texture*.—Smooth, glabrous.

*Luster*.—Matte.

*Color*.—RHS Yellow-Green 145A.

REPRODUCTIVE ORGANS

Stamens:

*Number*.—Average 3.

*Filament length*.—Average less than 0.5 mm.

*Filament color*.—RHS Yellow-Green 145D.

Anther:

*Shape*.—Oblong.

*Length*.—Average 1.75 mm.

*Width*.—Average 0.5 mm.

*Color*.—RHS Yellow-Green 152D.

*Pollen*.—None.

Pistil.—Number: Average 1. Length: Average 0.7 cm.

*Stigma*.—Shape: Feather-like, cleft. Length: Average 0.5 cm. Diameter: Average 0.5 mm. Color: RHS Greyed-Purple N186C.

*Style*.—Length: Average: 0.2 cm. Color: RHS Yellow-Green 145D. Ovary color: RHS Yellow-Green 145D.

OTHER CHARACTERISTICS

Fruit and seed: Not observed.

Disease and pest resistance: Similar resistance and susceptibility to pests and diseases of other *Pennisetum advena* varieties.

Temperature tolerance: Observed to tolerate temperatures up to 35° C. USDA zones 6 to 9.

Rain/wind tolerance: High tolerance to rain and wind.

What is claimed is:

1. A new and distinct cultivar of *Pennisetum* plant named 'TUS022' as herein illustrated and described.

* * * * *